United States Patent
Chodkowski et al.

(10) Patent No.: US 10,702,667 B2
(45) Date of Patent: Jul. 7, 2020

(54) HEADGEAR WITH A HYDROPHILIC WICKING MATERIAL

(71) Applicant: KONINKLIJKE PHILIPS N.V., Eindhoven (NL)

(72) Inventors: Lauren Patricia Chodkowski, Pittsburgh, PA (US); Richard Thomas Haibach, Verona, PA (US); Sandy Jane Shafer, Pittsburgh, PA (US)

(73) Assignee: Koninklijke Philips N.V., Eindhoven (NL)

(*) Notice: Subject to any disclaimer, the term of this patent is extended or adjusted under 35 U.S.C. 154(b) by 1071 days.

(21) Appl. No.: 15/039,904

(22) PCT Filed: Dec. 1, 2014

(86) PCT No.: PCT/IB2014/066476
§ 371 (c)(1),
(2) Date: May 27, 2016

(87) PCT Pub. No.: WO2015/083060
PCT Pub. Date: Jun. 11, 2015

(65) Prior Publication Data
US 2016/0375214 A1    Dec. 29, 2016

Related U.S. Application Data

(60) Provisional application No. 61/910,534, filed on Dec. 2, 2013.

(51) Int. Cl.
*A61M 16/06*       (2006.01)
*B32B 3/26*        (2006.01)
(Continued)

(52) U.S. Cl.
CPC .... *A61M 16/0683* (2013.01); *A61M 16/0633* (2014.02); *B32B 3/266* (2013.01);
(Continued)

(58) Field of Classification Search
CPC .... A61M 16/06–0655; A61M 16/0683; A61M 16/0694; A61M 2016/0661; A61M 602/14
See application file for complete search history.

(56) References Cited

U.S. PATENT DOCUMENTS 7,842,625 B1 * 11/2010  Stockton ............... D06M 13/02
                                                          442/164
2006/0042326 A1    3/2006  Hubner
(Continued)

FOREIGN PATENT DOCUMENTS

JP       2006264309 A    10/2006
WO     WO2009026627 A1   3/2009
(Continued)

*Primary Examiner* — Timothy A Stanis
*Assistant Examiner* — Charles M Vivian
(74) *Attorney, Agent, or Firm* — Michael W. Haas

(57) ABSTRACT

A headgear component for a patient interface device includes a member having a first surface and a second surface opposite the first surface, the member including at least one of a textile material and a foam material, the member having a plurality of vent holes extending therethrough, and a plurality of moisture wicking members provided on the first surface, the moisture wicking members covering the vent holes and being made of a hydrophilic material.

14 Claims, 8 Drawing Sheets

(51) Int. Cl.
   *B32B 3/30*    (2006.01)
   *B32B 5/18*    (2006.01)
   *B32B 5/24*    (2006.01)
   *B32B 27/12*   (2006.01)
   *B32B 27/28*   (2006.01)

(52) U.S. Cl.
   CPC ............. *B32B 3/30* (2013.01); *B32B 5/18* (2013.01); *B32B 5/245* (2013.01); *B32B 27/12* (2013.01); *B32B 27/283* (2013.01); *A61M 2205/0238* (2013.01); *A61M 2205/7527* (2013.01); *A61M 2207/00* (2013.01); *B32B 2307/728* (2013.01); *B32B 2535/00* (2013.01); *D10B 2401/022* (2013.01); *D10B 2509/00* (2013.01)

(56) References Cited

U.S. PATENT DOCUMENTS

| | | |
|---|---|---|
| 2007/0181135 A1 | 8/2007 | Baker |
| 2008/0254263 A1 | 10/2008 | Yasui |
| 2009/0044810 A1 | 2/2009 | Kwok |
| 2009/0104404 A1 | 4/2009 | Polegato Moretti |
| 2011/0104448 A1 | 5/2011 | Chung |
| 2013/0061366 A1* | 3/2013 | Pezzimenti ............ A41D 31/02 2/69 |
| 2013/0112203 A1 | 5/2013 | Henry |
| 2013/0263859 A1* | 10/2013 | Ho ................... A61M 16/0683 128/206.21 |

FOREIGN PATENT DOCUMENTS

| | | |
|---|---|---|
| WO | WO2013001438 A1 | 1/2013 |
| WO | WO2013001487 A1 | 1/2013 |

\* cited by examiner

HEADGEAR WITH A HYDROPHILIC WICKING MATERIAL

CROSS-REFERENCE TO RELATED APPLICATIONS

This patent application claims the priority benefit under 35 U.S.C. § 371 of international patent application no PCT/IB2014/066476, filed Dec. 1, 2014, which claims the priority benefit under 35 U.S.C. § 119(e) of U.S. Provisional Application No. 61/910,534 filed on Dec. 2, 2013, the contents of which are herein incorporated by reference.

BACKGROUND OF THE INVENTION

1. Field of the Invention

The present invention pertains to patient interface devices structured to deliver a flow of breathing gas to a patient, and, in particular, to patient interface devices employing a headgear component having a hydrophilic moisture wicking system.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, a nasal cushion that rests beneath the patient's nose (such as a "pillows" style nasal cushion having nasal prongs that are received within the patient's nares or a "cradle" style nasal cushion that rests beneath and covers the patient's nares), or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient.

It is known to maintain such devices on the face of a wearer by a headgear having one or more straps adapted to fit over/around the patient's head. The headgear typically wraps around the patient's head (coming in contact with the patient's hair and face) in order to apply the necessary forces normal to the face to achieve a suitable seal. Most headgear used in non-invasive ventilation and pressure support therapies is made from a foam laminate material that typically includes: (i) a middle foam layer made of, for example, a resiliently stretchable open-celled polyurethane foam, (ii) an outer fabric layer made of, for example, a resiliently stretchable loop fabric, such as a blend of nylon and spandex, and (iii) an inner fabric layer made of, for example, a resiliently stretchable wicking fabric, such as a blend of polyester and spandex. Foam laminate materials retain heat well and can be uncomfortably hot for overnight use. In fact, many patients complain of sweating from the headgear they use during therapy. In addition, another common complaint of current headgear is that it slips around on the head as the patient moves around, sometimes even slipping off the head and interfering with treatment.

SUMMARY OF THE INVENTION

In one embodiment, a headgear component for a patient interface device is provided that includes a member having a first surface and a second surface opposite the first surface, the member including at least one of a textile material and a foam material, the member having a plurality of vent holes extending therethrough, and a plurality of moisture wicking members provided on the first surface, the moisture wicking members covering the vent holes and being made of a hydrophilic material.

In another embodiment, a method of making a headgear component for a patient interface device includes providing a member having a first surface and a second surface opposite the first surface, the member including at least one of a textile material and a foam material, forming a plurality of vent holes in the member that extend through the member, and forming a plurality of moisture wicking members on the first surface, the moisture wicking members covering the vent holes and being made of a hydrophilic material.

DETAILED DESCRIPTION OF EXEMPLARY EMBODIMENTS

Figure 1:
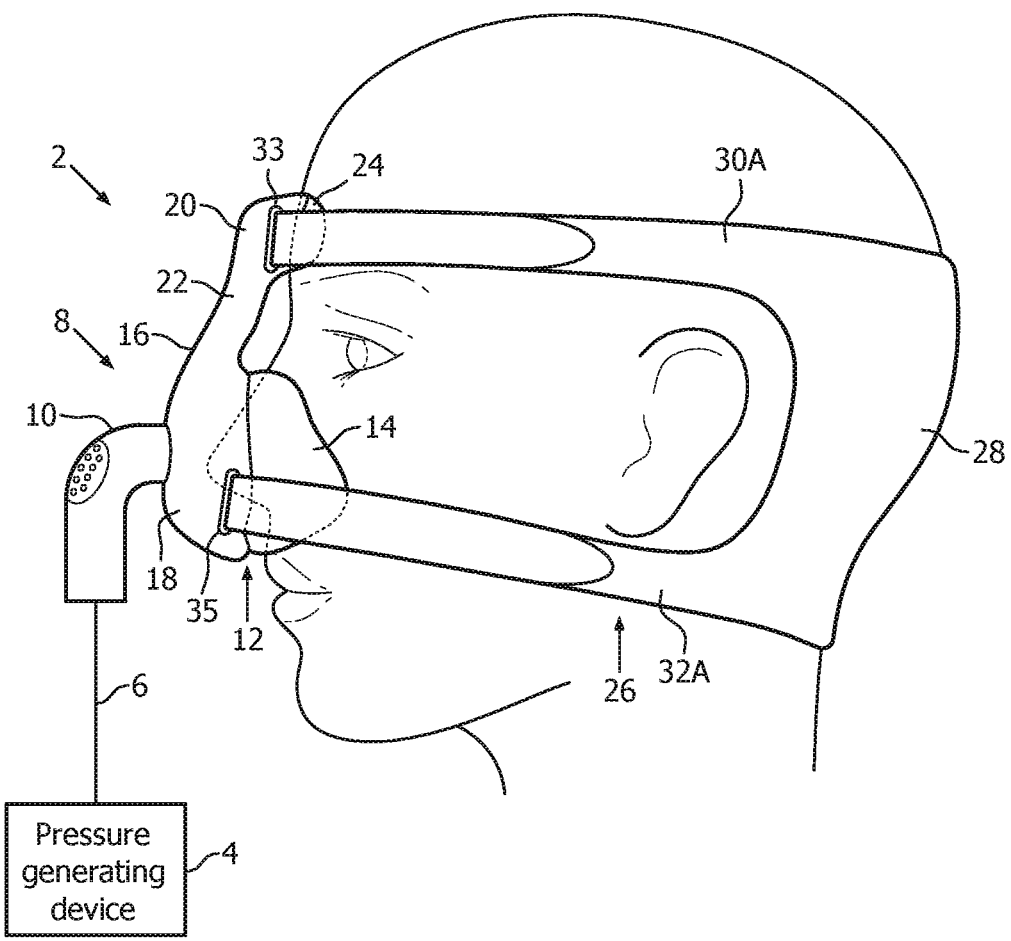
FIG. 1 is a schematic diagram of a system adapted to provide a regimen of respiratory therapy to a patient according to one exemplary embodiment.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "hydrophilic" shall mean having at least 10% water uptake (based on total weight) over 8 hours. As used herein, the term "textile" shall mean a material consisting of a network of interlaced or otherwise entangled natural or artificial fibers made by, for example and without limitation, weaving, knitting, spreading, crocheting, or bonding (e.g., by chemical, mechanical, heat or solvent treatment) the fibers to form the network, and may include, for example, and without limitation, woven and nonwoven fabric materials.

As used herein, the term "foam" shall mean a substance that is formed by trapping pockets of gas in a solid material, and may include closed-cell foams wherein the gas forms discrete pockets each completely surrounded by the solid material, and open-cell foams, wherein the gas pockets connect with each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIG. 1. System 2 includes a pressure generating device 4, a delivery conduit 6, and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

In the exemplary embodiment, patient interface 8 includes a patient sealing assembly 12, which in the illustrated embodiment is a nasal mask. However, other types of patient sealing assemblies, such as, without limitation, a nasal/oral mask, a nasal cushion, or a full face mask, which facilitate the delivery of the flow of breathing gas to the airway of a patient may be substituted for patient sealing assembly 12 while remaining within the scope of the present invention. Patient sealing assembly 12 includes a cushion 14 coupled to a frame member 16. In the illustrated embodiment, cushion 14 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, frame member 16 is made of a rigid or semi-rigid material, such as, without limitation, an injection molded thermoplastic or silicone, and includes a faceplate portion 18 to which cushion 14 is fluidly attached. An opening in faceplate portion 18, to which fluid coupling conduit 10 is coupled, allows the flow of breathing gas from pressure generating device 4 to be communicated to an interior space defined by cushion 14, and then to the airway of a patient.

Frame member 16 also includes a forehead support member 20 that is coupled to the faceplate portion by a connecting member 22. A forehead cushion 24 is coupled to the rear of forehead support member 20. In the exemplary embodiment, forehead cushion 24 is made of a material that is similar to the material of cushion 14.

Figure 2:
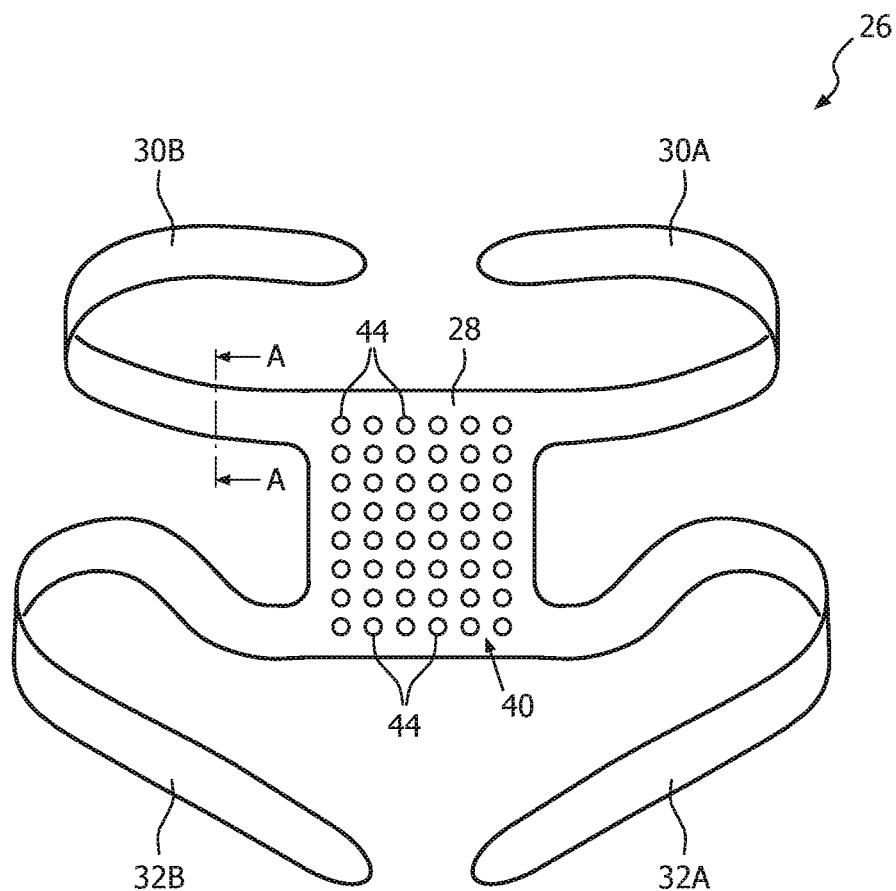
FIG. 2 is a front elevational view and FIG. 3 is a rear elevational view of a headgear component forming part of the system of FIG. 1.
Figure 3:
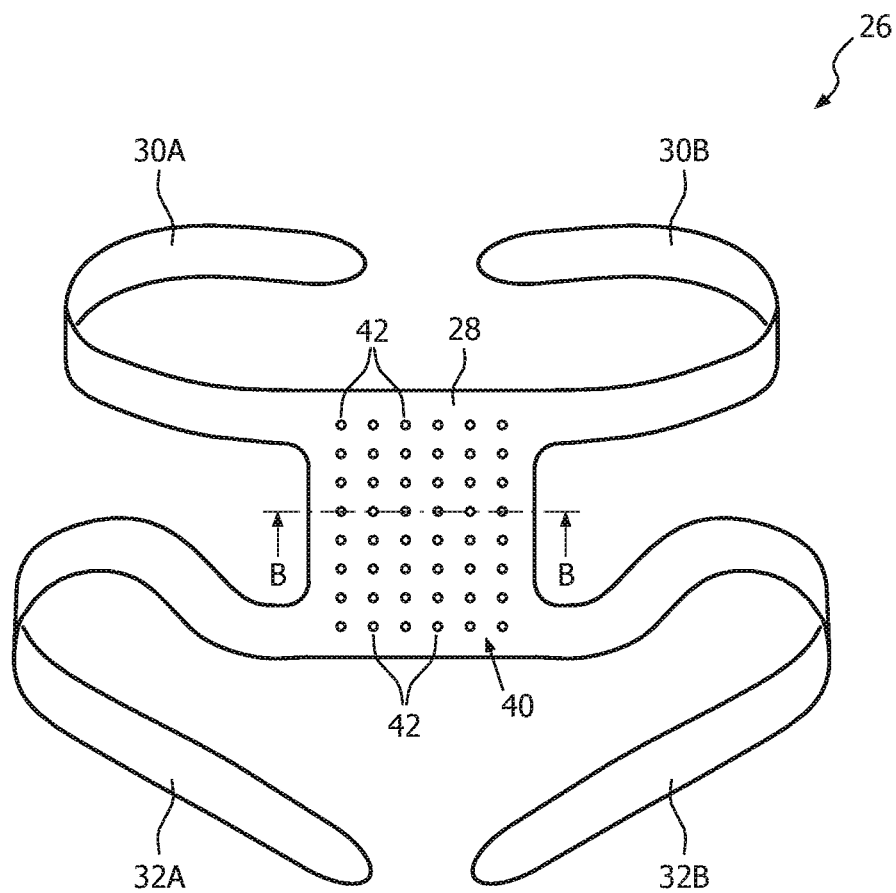

Patient interface 8 also includes a headgear component 26 for securing patient interface device 8 to the patient's head. FIG. 2 is a front elevational view and FIG. 3 is a rear elevational view of headgear component 26 according to the exemplary embodiment. Headgear component 26 includes a back member 28, upper strap members 30A, 30B, and lower strap members 32A, 32B. Upper strap members 30A, 30B extend from an upper portion of back member 28 and are structured to extend toward frame member 16 above the patient's ears as seen in FIG. 1 and be coupled to forehead support member 20. More specifically, in the exemplary embodiment, each upper strap member 30A, 30B includes a hook and loop fastening system, such as VELCRO®, provided on the end thereof. Each upper strap member 30A, 30B may thus be threaded through respective looped portions 33 provided on opposites sides of forehead support member 20 and then be bent back on itself in order to adhere the hook fastener portion to the loop fastener portion and thereby adjustably connect upper strap member 30A, 30B to forehead support member 20. Lower strap members 32A, 32B extend from a lower portion of back member 28 and are structured to extend toward frame member 16 below the patient's ears.

As seen in FIG. 1, in the exemplary, non-limiting embodiment, each lower strap member 32A, 32B, like each upper strap member 30A, 30B, includes a hook and loop fastening system, such as VELCRO®, provided on the end thereof. Each lower strap member 32A, 32B may thus be threaded through respective looped portions 35 provided on opposites sides of faceplate portion 18 and then be bent back on itself in order to adhere the hook fastener portion to the loop fastener portion and thereby adjustably connect lower strap member 32A, 32B to faceplate portion 18. It will be understood that the described hook and loop fastening arrangement is meant to be exemplary only, and that other selectively adjustable fastening arrangements are also possible within the scope of the present invention.

Figure 4:
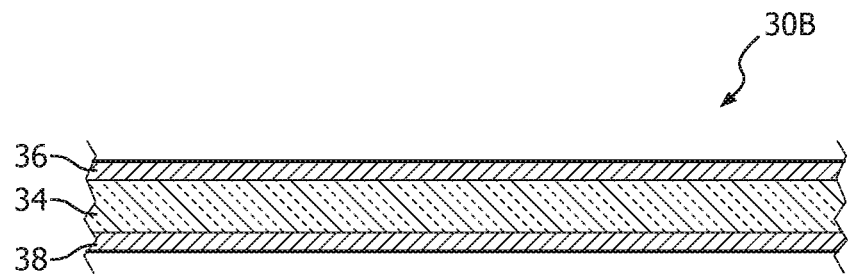
FIG. 4 is a cross-sectional view taken along lines A-A of FIG. 2.

In addition, headgear component 26 is, in the exemplary embodiment, formed from a foam laminate material. In particular, as shown in FIG. 4, which is a cross-sectional view of headgear component 26 taken along lines A-A of FIG. 2, headgear component 26 is formed from a foam laminate material that includes: (i) a central layer 34 made of a foam material, such as, without limitation, a resiliently stretchable open-celled polyurethane foam, (ii) an outer layer 36 made of first textile material, such as, without limitation, a resiliently stretchable loop fabric (e.g., a blend of nylon and spandex), and (iii) an inner layer 38 (i.e., a skin contacting layer) made of made of second textile material, such as, without limitation, a resiliently stretchable wicking fabric (e.g., a blend of polyester and spandex).

Figure 5:
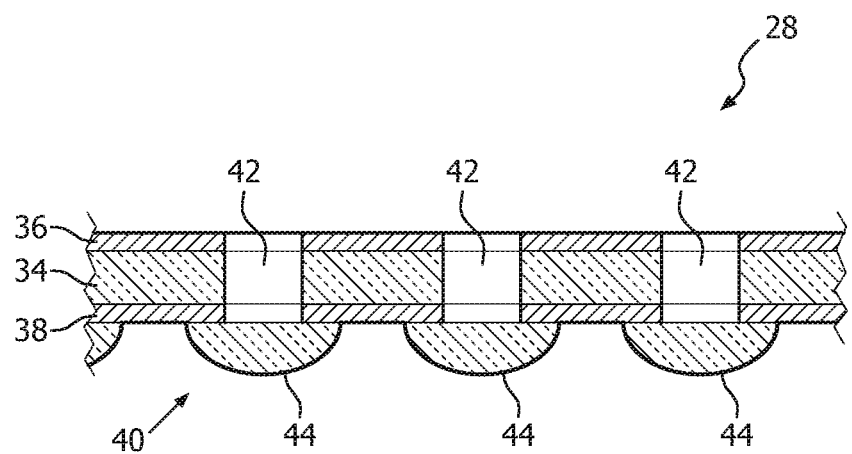
FIG. 5 is a cross-sectional view taken along lines B-B of FIG. 3.

Furthermore, as shown in FIGS. 2, 3 and 5, which is a cross-sectional view of headgear component 26 taken along lines B-B of FIG. 3, headgear component 26 is provided with a moisture wicking system 40 in back member 28. Moisture wicking system 40 is structured to (i) wick moisture away from the skin of the patient so that it can be vented to atmosphere for evaporation (which helps to cool the region around headgear component 26 and prevent the accumulation of sweat), and (ii) stabilize headgear component 26 by helping it to grip and stay in place as the patient moves around during therapy (e.g., during sleep).

In the exemplary embodiment, moisture wicking system 40 includes a plurality of vent holes 42 (formed in an array pattern) extending through the foam laminate material portion of back member 28 (FIGS. 3 and 5). For example, in one embodiment, vent holes 42 are about 1 mm diameter cylindrical holes die-cut into the foam laminate. In the exemplary embodiment, moisture wicking system 40 also includes a plurality of separate and distinct moisture wicking caps 44 (formed in an array pattern) provided on the external surface of inner layer 38 (FIGS. 2 and 4). Moisture wicking caps 44 are made of a hydrophilic polymer material, such as, without limitation, hydrophilic silicone. In the exemplary embodiment, moisture wicking caps 44 are made of hydrophilic silicone having a durometer of 5 Shore A to 60 Shore A. In addition, each of the moisture wicking caps 44 is provided on top of and covers a respective one of the vent holes 42. In the exemplary embodiment, moisture wicking caps 44 are dome-shaped structures (although other shapes are possible) having a based diameter of about 2 mm, and are screen printed on the external surface of inner layer 38.

In operation, moisture wicking caps 44 draw moisture away from the skin of the patient and direct the moisture to vent holes 42. Vent holes 42 allow the moisture to come in contact with the atmosphere and evaporate quickly. Moisture wicking caps 44 also lightly grip hair and skin so as to keep headgear component 26 in a proper position as the patient moves around at night.

Figure 6A:
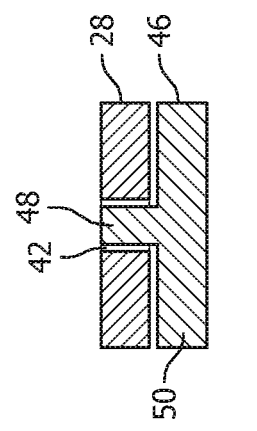
FIGS. 6A through 6D schematically illustrate one exemplary method for producing the headgear component of FIGS. 1-5.
Figure 6B:
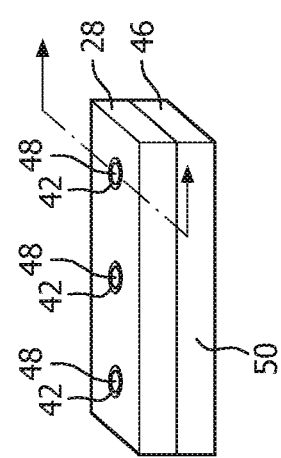
Figure 6C:
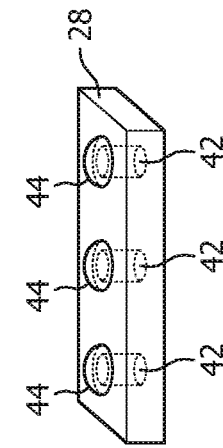
Figure 6D:
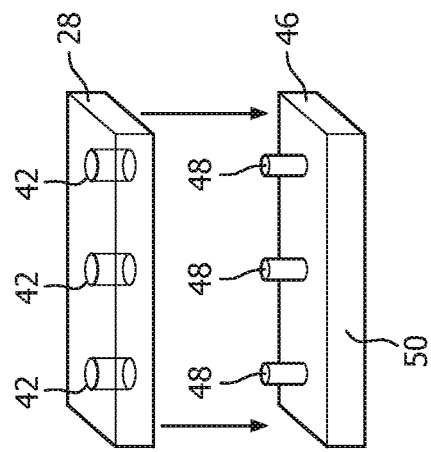

FIGS. 6A through 6D schematically illustrate one exemplary method for producing headgear component 26 having moisture wicking system 40. For ease of illustration, only a portion of headgear component 26, and in particular back member 28, is shown schematically in FIGS. 6A through 6D. First, vent holes 42 are provided on the foam laminate, for example by die-cutting. Then, as shown in FIGS. 6A to 6C, back member 28 is fit onto a metal fixture 46 (a portion thereof is shown in the FIGS.) having a plurality of pins 48 extending upwardly from a base member 50. Pins 48 are positioned on base member 50 in a pattern that matches the pattern of vent holes 42 such that they are able to be aligned with and received within the vent holes 42 (FIGS. 6B and 6C). Next, as shown in FIG. 6D, moisture wicking caps 44 are screen printed over vent holes 42. During that process, pins 48 keep vent holes 42 from completely filling with the hydrophilic material forming moisture wicking caps 44. Also, pins 48 act to locate back member 28 so that moisture wicking caps 44 line up exactly with vent holes 42 and cap them completely. As also shown in FIG. 6D, after wicking caps 44 are so provided, headgear component 26 having moisture wicking system 40 is removed from metal fixture 46.

Figure 7:
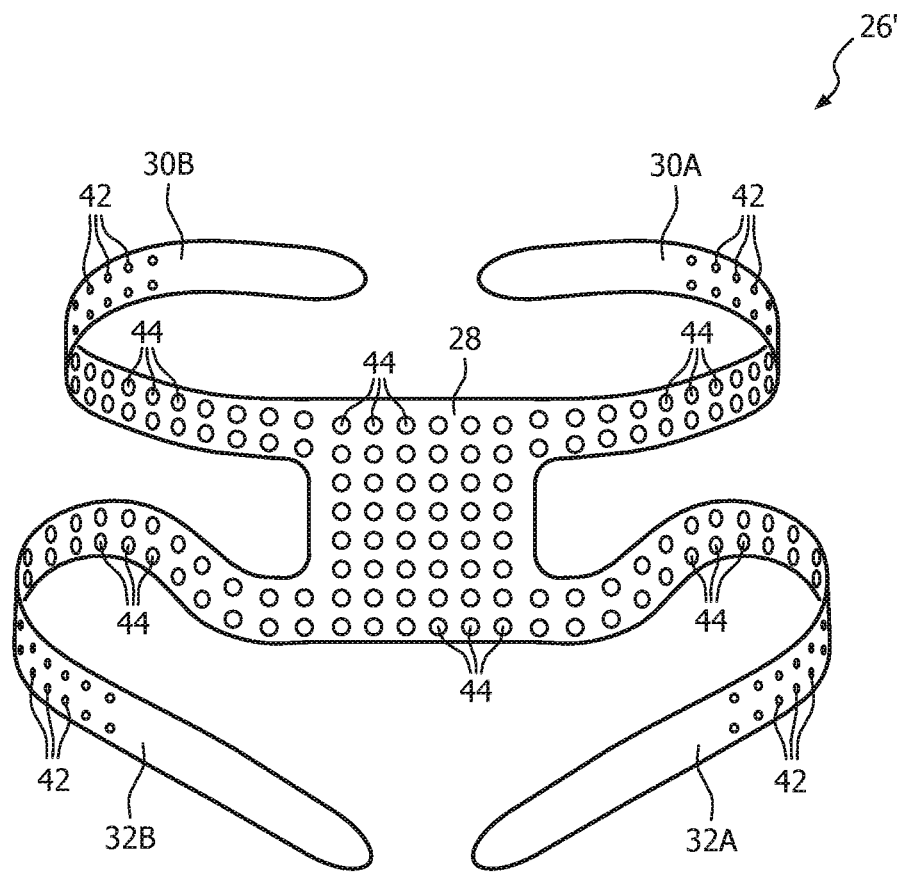
FIG. 7 is a front elevational view of a headgear component according to an alternative exemplary embodiment.

Moreover, the embodiment shown in FIGS. 1-5 in which moisture wicking system 40 is provided only on back member 28 is mean to be exemplary only, and it will be understood that moisture wicking system 40 may be provided on other portions of the headgear. For example, FIG. 7 is a front elevational view of a headgear component 26' according to an alternative exemplary embodiment. Headgear component 26' is similar to headgear component 26, except that moisture wicking system 40 is also provided on upper strap member 30A, 30B and lower strap members 32A, 32B. Still other configurations are also possible within the scope of the present invention.

Figure 8:
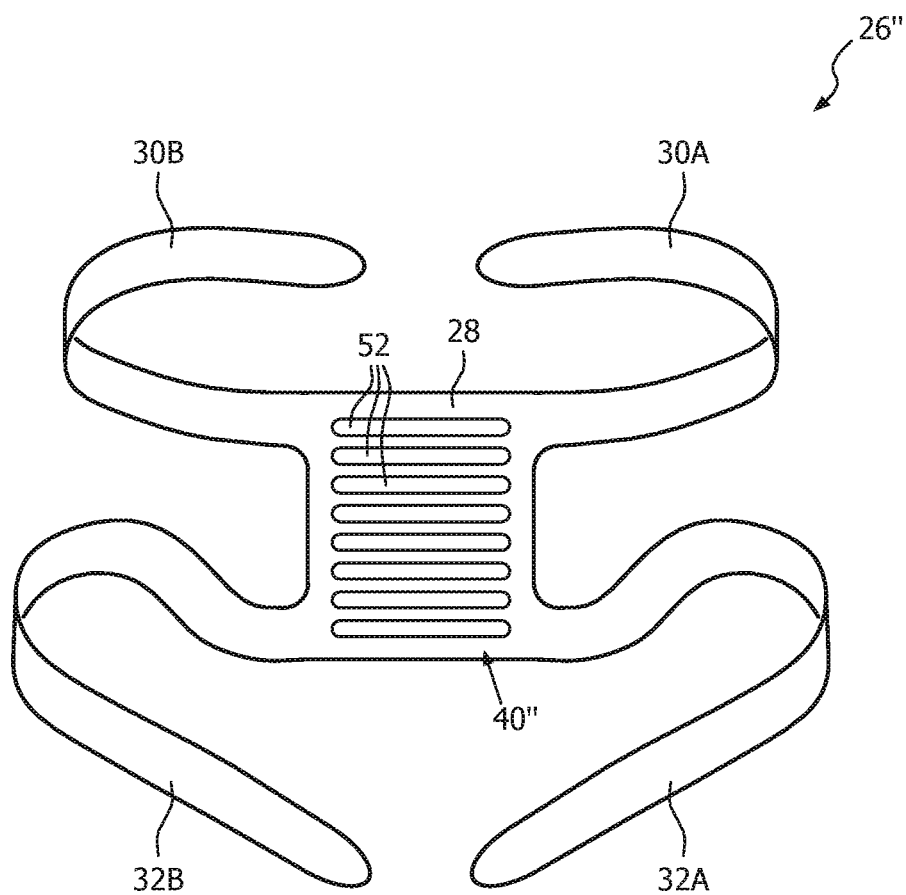
FIG. 8 is a front elevational view of a headgear component according to another alternative exemplary embodiment.
Figure 9:
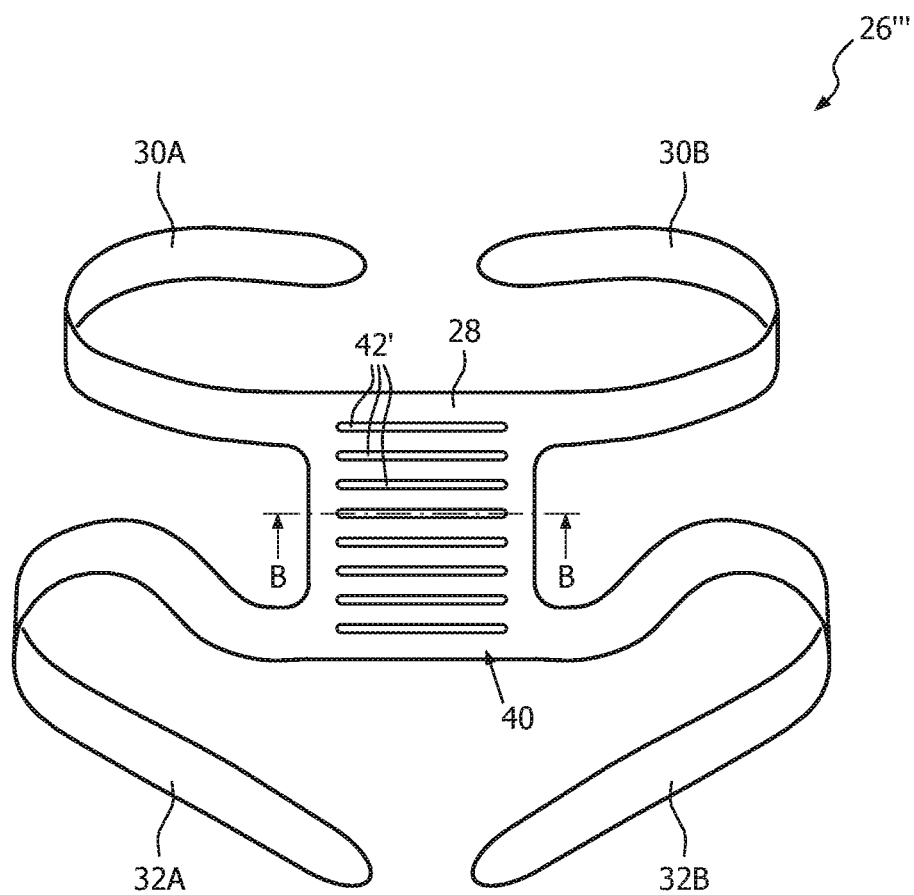
FIG. 9 is a rear elevational view of a headgear component according to still another alternative exemplary embodiment.

In addition, in the embodiments shown in FIGS. 1-5 and 7, moisture wicking system 40 includes a plurality of separate and distinct moisture wicking caps 44 provided on top of and covering respective vent holes 42. FIG. 8 is a front elevational view of a headgear component 26" according to an alternative exemplary embodiment that includes an alternative moisture wicking system 40" wherein the separate and distinct moisture wicking caps 44 are replaced by a plurality of moisture wicking members 52 arranged in rows. As seen in FIG. 8, each moisture wicking member 52 is a wider elongate linear pad member that covers a plurality of the vent holes 42. In still another alternative, the vent holes 42 may be elongated and linear (formed in rows) as shown in FIG. 9 in connection with headgear component 26''' such that each moisture wicking member 52 covers only a respective one of the alternative vent holes (labeled 42'). Still other geometries and patterns of the wicking members and vent holes are possible within the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A headgear component for a patient interface device, comprising:
   a member having a first surface and a second surface opposite the first surface, the member including at least one of a textile material and a foam material, the member having a plurality of vent holes extending therethrough; and
   a plurality of moisture wicking members provided on the first surface, the plurality of moisture wicking members covering the plurality of vent holes and being made of a hydrophilic polymer, wherein the plurality of moisture wicking members are each separate and distinct from one another such that the plurality of moisture wicking members are not a unitary structure.

2. The headgear component according to claim 1, wherein the hydrophilic polymer is hydrophilic silicone.

3. The headgear component according to claim 1, wherein the member comprises the textile material and the foam material, wherein the textile material is a fabric laminate material.

4. The headgear component according to claim 3, wherein the foam material is a central layer wherein the textile material comprises an outer layer made of first textile material and provided on a first side of the central layer, and an inner layer made of second textile material and provided on a first side of the central layer.

5. The headgear component according to claim 1, wherein the plurality of moisture wicking members comprise a plurality of separate and distinct cap members, each of the plurality of separate and distinct cap members being provided on and covering a respective one of the plurality of vent holes.

6. The headgear component according to claim 5, wherein each of the plurality of separate and distinct cap members is a dome-shaped cap member.

7. The headgear component according to claim 1, wherein the plurality of moisture wicking members comprise a plurality of linear elongated members, wherein each of the plurality of vent holes is linear and elongated, and wherein each of the plurality of linear elongated members is provided on and covers a respective one of the plurality of vent holes.

8. The headgear component according to claim 1, wherein the plurality of moisture wicking members comprise a plurality of linear elongated members, and wherein each of the plurality of linear elongated members is provided on and covers a subset of the plurality of vent holes.

9. The headgear component according to claim 1, wherein the member is a back member.

10. The headgear component according to claim 1, wherein the member is a strap member.

11. A method of making a headgear component for a patient interface device, comprising:

providing a member having a first surface and a second surface opposite the first surface, the member including at least one of a textile material and a foam material;

forming a plurality of vent holes in the member that extend through the member; and forming a plurality of moisture wicking members on the first surface, the plurality of moisture wicking members covering the plurality of vent holes and being made of a hydrophilic polymer, wherein the plurality of of moisture wicking members are not a unitary structure.

12. A method of making a headgear component for a patient interface device, comprising:

providing a member having a first surface and a second surface opposite the first surface, the member including at least one of a textile material and a foam material, forming a plurality of vent holes in the member that extend through the member, and forming a plurality of moisture wicking members on the first surface, the plurality of moisture wicking members covering the plurality of vent holes and being made of a hydrophobic polymer, wherein the forming a plurality of moisture wicking members comprises:

positioning the member on a fixture having a plurality of pins extending upwardly from a base member, wherein the plurality of pins are positioned on the base member in a pattern that matches a pattern of the plurality of vent holes such that the plurality of pins are aligned with and received within the plurality of vent holes; and forming the plurality of moisture wicking members on the first surface when the member is positioned on the fixture.

13. The method according to claim 12, wherein the forming the plurality of moisture wicking members on the first surface comprises screen printing the plurality of moisture wicking members on the first surface.

14. The method according to claim 11, wherein the forming the plurality of vent holes in the member comprises die-cutting the plurality of vent holes in the member.

* * * * *